United States Patent [19]

Chang et al.

[11] Patent Number: 5,032,728
[45] Date of Patent: Jul. 16, 1991

[54] SINGLE PHOTON EMISSION COMPUTED TOMOGRAPHY SYSTEM

[75] Inventors: Wei Chang; Peter Kirchner, both of Iowa City, Iowa

[73] Assignee: The University of Iowa Research Foundation, Iowa City, Iowa

[21] Appl. No.: 269,440

[22] Filed: Nov. 9, 1988

[51] Int. Cl.$^5$ .......................... G01T 1/164; G01T 1/20
[52] U.S. Cl. .......................... 250/363.04; 250/363.01; 250/363.03; 250/363.10; 250/367
[58] Field of Search ..................... 250/363.02, 363.031, 250/363.05, 363.01, 363.10, 367

[56] References Cited

U.S. PATENT DOCUMENTS

| | | | |
|---|---|---|---|
| 4,150,292 | 4/1979 | Ter-Poggosian | 250/363 S |
| 4,389,569 | 6/1983 | Hattori et al. | 250/363 S |
| 4,584,478 | 4/1986 | Genna et al. | 250/363.1 X |
| 4,743,764 | 5/1988 | Casey et al. | 250/363 S |
| 4,748,328 | 5/1988 | Chang et al. | 250/363 R |
| 4,774,410 | 9/1988 | Hsien | 250/363.10 |
| 4,849,638 | 7/1989 | Hawman | 250/363.02 |

FOREIGN PATENT DOCUMENTS

| | | | |
|---|---|---|---|
| 60-214288 | 10/1985 | Japan | 250/363.1 |
| 2034148 | 5/1980 | United Kingdom | 250/363.1 |

OTHER PUBLICATIONS

Conrad et al., "The Scinticon a New Gamma Camera", Siemens Aktiengesellschaft Medical Engineering Group, 1973, pp. 220–225.
Williams et al., "Introducing SPRINT": A Single Photon Ring System for Emission Tomography, NS-29 I.E.E.E. Trans. Nucl. Sci. 628, (1979).
Wong et al., "Characteristics of Small Barium Fluoride (BaF) Scintillator for High Intrinsic Resolution Time-of-Flight Positron Emission Tomography," NS-31 I.E.E.E. Trans. Nucl. Sci 381 (1984).
Burnham et al., "Design of a Cylindrical Scintillation Camera for Positron Tomographs", NS-32 I.E.E.E. Trans. Nucl. Sci. 889 (1985)
Chang et al., "Design and Investigation of a Modular Focused Collimator Based Multiple Detector Ring System for SPECT Imaging of the Brain", 671 SPIE 200 (1986).
Casey et al., "A Multicrystal Two Dimensional BGO Detector System for Positron Emission Tomography", NS-33 I.E.E.E. Trans. Nucl. Sci. 460 (1986).
Genna et al., "The Development of Aspect, an Annular Single Crystal Brain Camera for High Efficiency SPECT", NS-35 I.E.E.E. Trans. Nucl. Sci. 654 (1988).
Rogers et al., "SPRINT II: A second Generation Ring-Geometry SPECT Instrument for Brain Imaging," 29 J. Nucl. Med. 760 (1988).

Primary Examiner—Constantine Hannaher
Assistant Examiner—Jacob M. Eisenberg
Attorney, Agent, or Firm—Pearson & Pearson

[57] ABSTRACT

A single photon emission computed tomography (SPECT) system for producing transaxial images in a plurality of transaxial planes through a body. The SPECT system includes a detector system with an in-plane spatial resolution that is determined by the in-plane spatial resolution of collimator modules disposed in a ring around the body to be imaged. Photo detectors and related circuits merely determine a po :ion in a photon detector matrix having discrete azimuthal positions that correspond to the physical size of a collimator module. Axial spatial resolution or slice thickness for the detector system is determined either by collimator modules or by collimator modules in conjunction with the intrinsic resolution of the photon detectors.

13 Claims, 6 Drawing Sheets

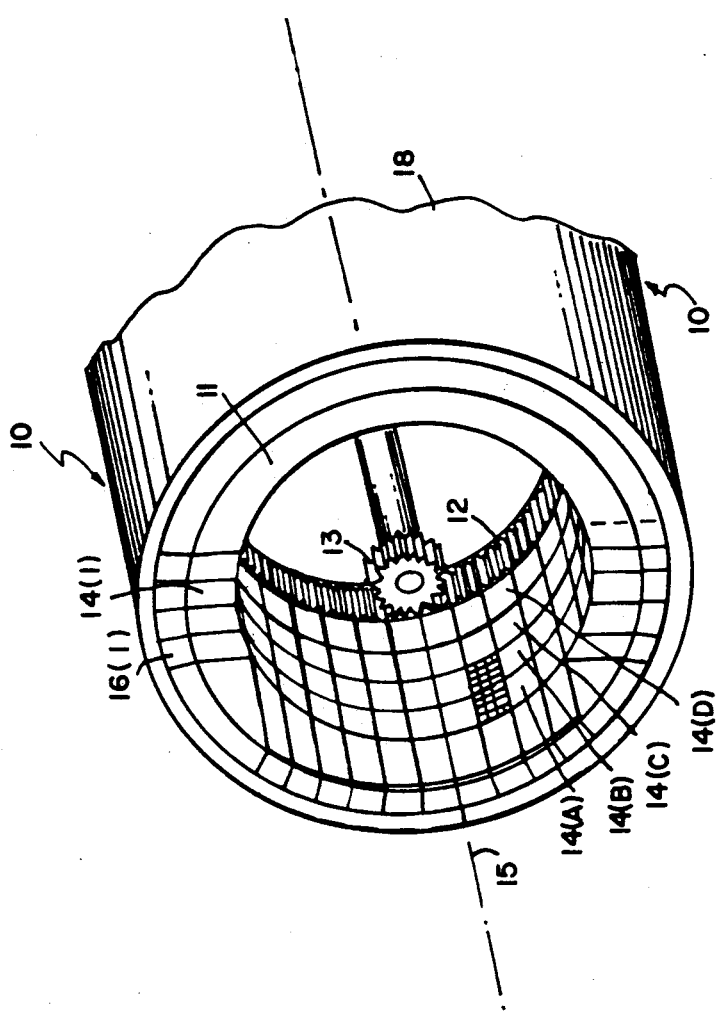
FIG.1A
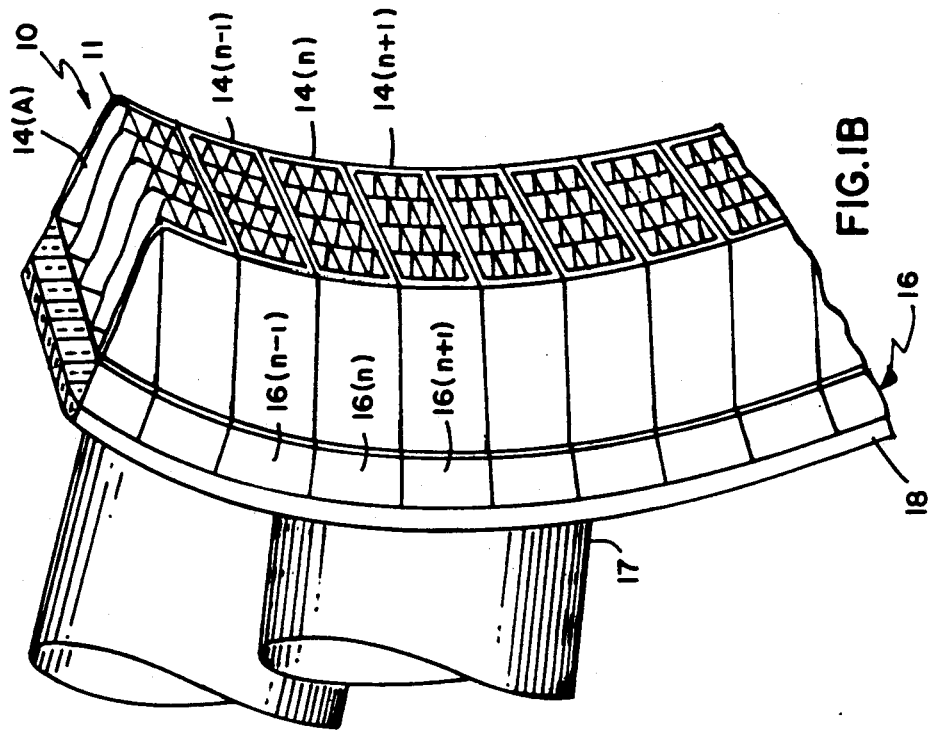
FIG.1B
FIG.1

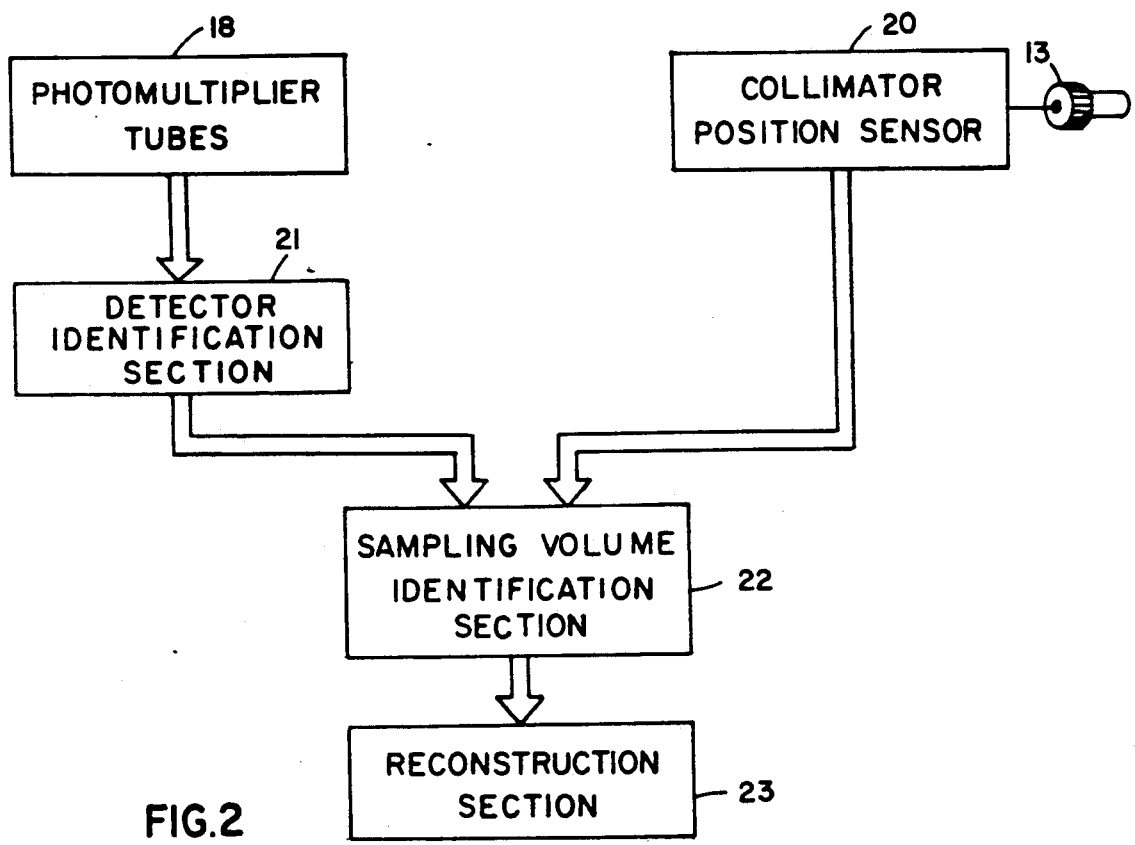
FIG.2
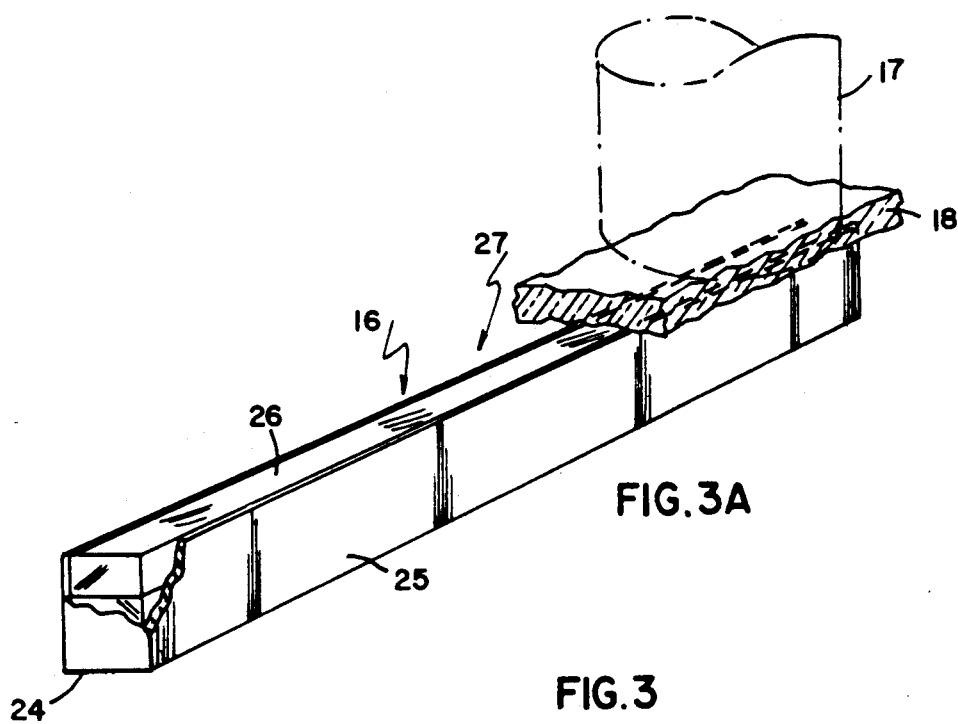
FIG.3A
FIG.3

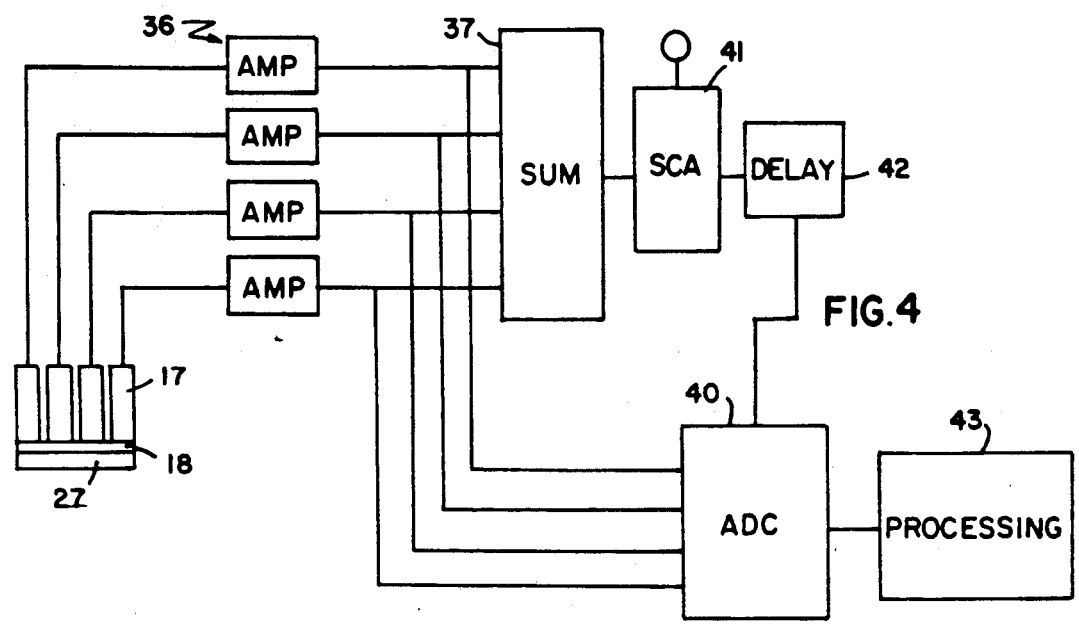
FIG. 4
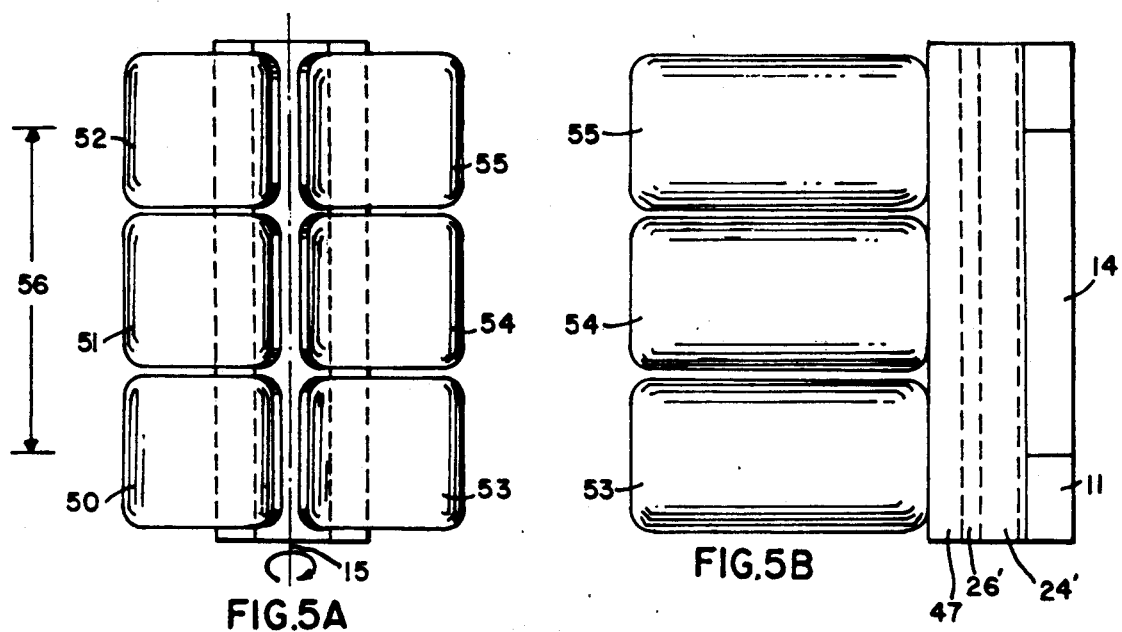
FIG. 5A
FIG. 5B
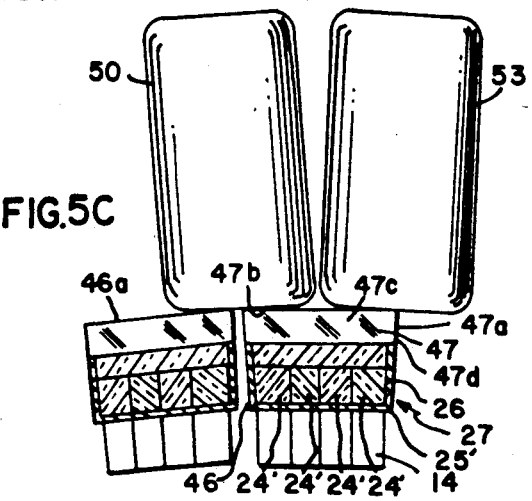
FIG. 5C
FIG. 5

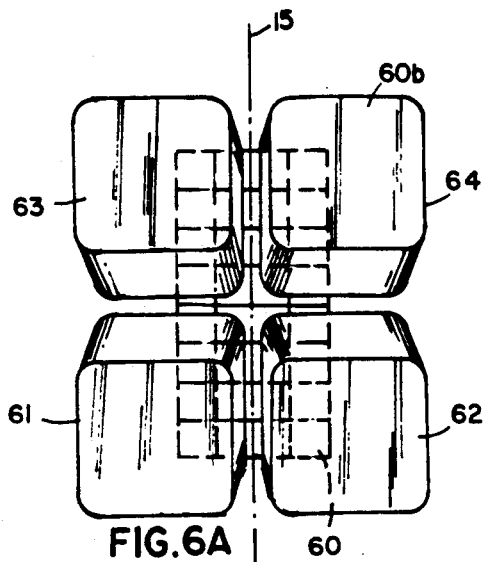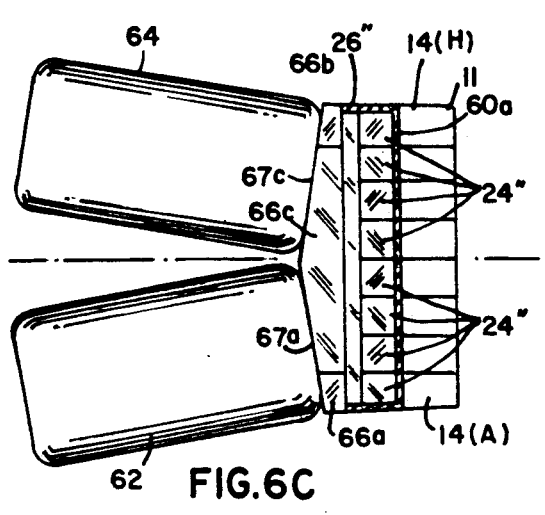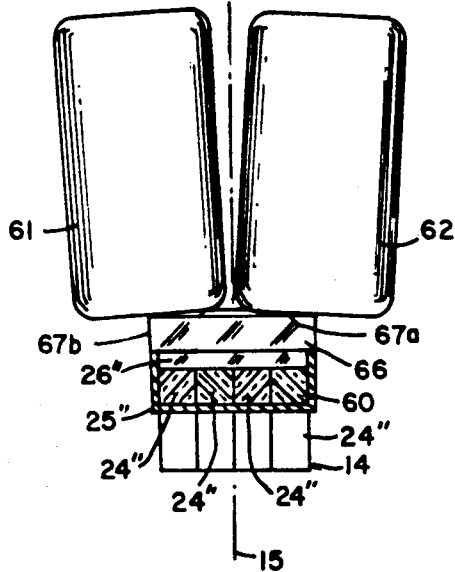
FIG. 6A
FIG. 6C
FIG. 6B
FIG. 6

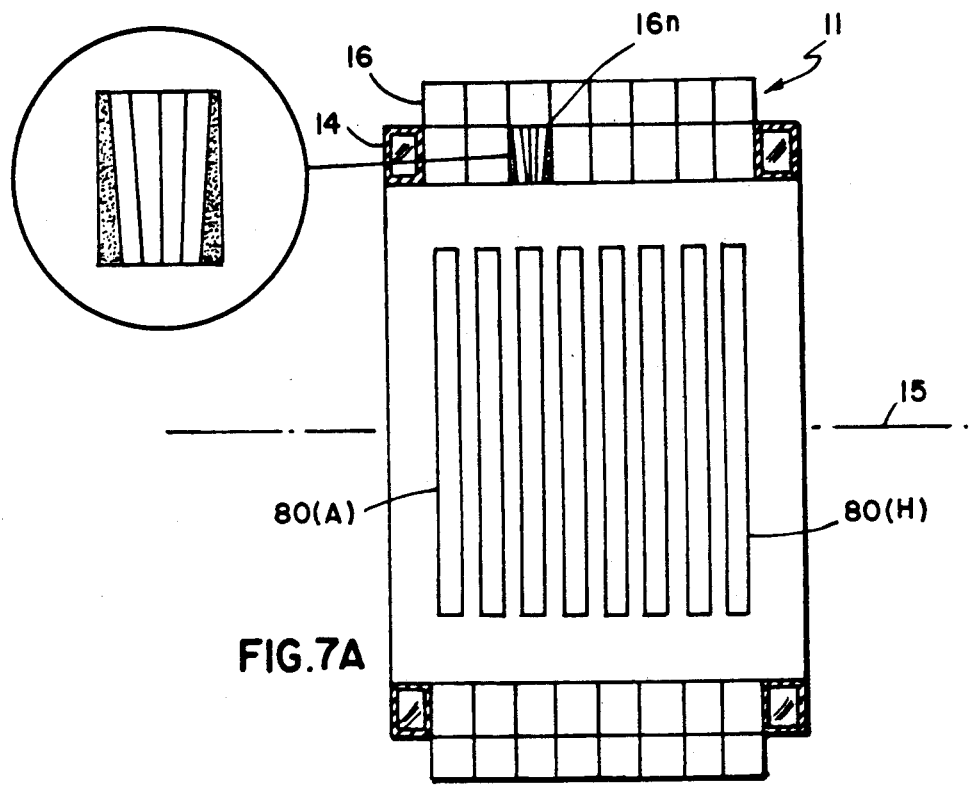
FIG. 7A
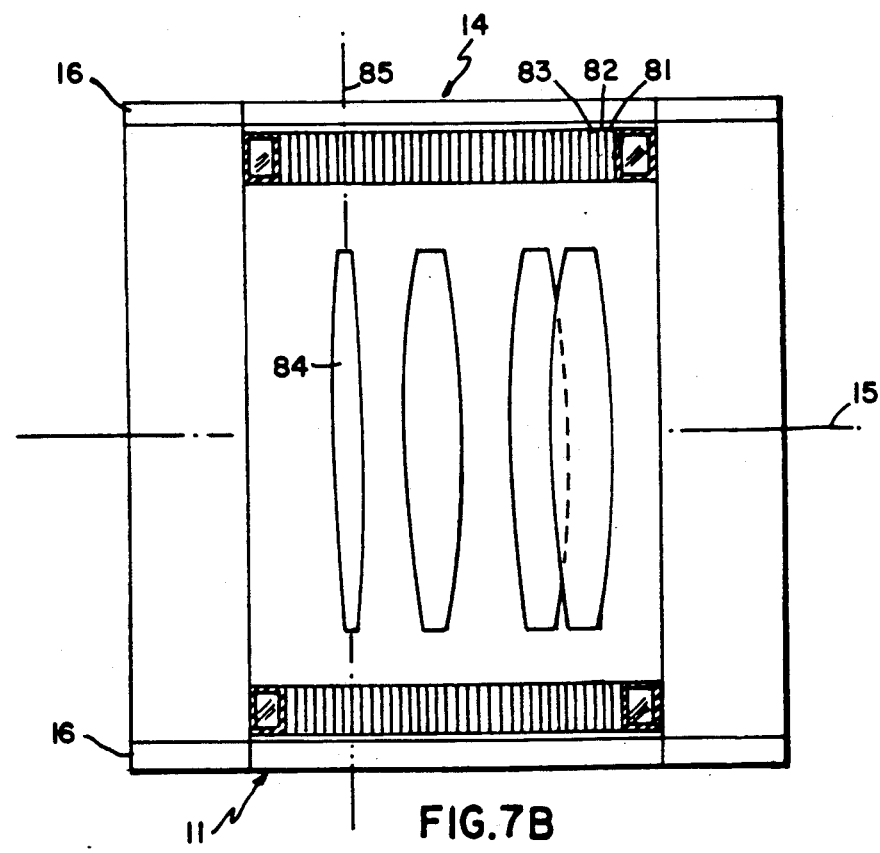
FIG. 7B
FIG. 7

SINGLE PHOTON EMISSION COMPUTED TOMOGRAPHY SYSTEM

BACKGROUND OF THE INVENTION

1. Field of Invention

This invention generally relates to single photon emission computed tomography (SPECT) systems and more specifically to multi-slice systems for acquiring image data from parallel, transaxial planes in tomographic slices.

2. References

Reference is made to the following United States Letters Patent and publications:

Ter-Pogossian, Imaging Device for Computerized Tomography, U.S. Pat. No. 4,150,292 (1979).

Williams et al, Introducing SPRINT: A Single Photon Ring System for Emission Tomography, NS-29 I.E.E.E. TRANS.NUCL.SCI. 628, (1979).

Hattori et al, Emission Computed Tomograph, U.S. Pat. No. 4,389,569 (1979).

Jaszczak et al, "SPECT: Single Photon Emission Computed Tomography", NS-27 I.E.E.E. Trans.Nucl.Sci. 1137 (1980)

Hirose et al, A Hybrid Emission CT Headtome II, NS-29 I.E.E.E. Trans.Nucl.Sci. 520 (1982).

Milster et al, A Modular Scintillation Camera For Use in Nuclear Medicine, NS-31 I.E.E.E. Trans.Nucl.Sci. 578, (1984).

Wong et al, Characteristics of Small Barium Fluoride (BaF) Scintillator for High Intrinsic Resolution Time-of-Flight Positron Emission Tomography, NS-31 I.E.E.E. Trans.Nucl.Sci. 381 (1984).

Burnham et al, Design of a Cylindrical Scintillation Camera for Positron Tomographs, NS-32 I.E.E.E. Trans.Nucl.Sci. 889 (1985).

Lim et al, Triangular SPECT System for 3-D Total Organ Volume Imaging: Design Concept and Preliminary Imaging Result, NS-32 I.E.E.E. Trans.Nucl.Sci. 741 (1985)

Casey et al, A Multicrystal Two Dimensional BGO Detector System for Positron Emission Tomography, NS-33 I.E.E.E. Trans.Nucl.Sci. 460 (1986).

Chang et al, Design and Investigation of a Modular Focused Collimator Based Multiple Detector Ring System for SPECT Imaging of the Brain, 671 SPIE 200 (1986).

Genna et al, Radionuclide Annular Single Crystal Scintillator Camera with Rotating Collimator, U.S. Pat. No. 4,584,478 (1986).

Casey et al, Two Dimensional Photon Counting Position Encoder System and Process, U.S. Pat. No. 4,743,764 (1988).

Chang et al, Single Photon Emission Computed tomograph Using Focused Modular Collimators, U.S. Pat. No. 4,748,328 (1988).

Genna et al, The Development of Aspect, an Annular Single Crystal Brain Camera for High Efficiency SPECT, NS-35 I.E.E.E. Trans.Nucl.Sci. 654 (1988).

Rogers et al, SPRINT II: A Second Generation Ring-Geometry SPECT Instrument for Brain Imaging, 29 J.Nucl.Med. 760 (1988).

3. Description of Related Art

Single Photon Emission Computed Tomography (SPECT) and Positron Emission Tomography (PET) are two imaging techniques for the noninvasive imaging of a distribution of tracers in accordance with a physiological function, particularly in humans. Both systems generate tomographic images that represent the distribution of a radioisotope in one or more transaxial, and normally transverse, thin planar sections through a portion of the anatomy, such as the brain or heart. This distribution corresponds qualitatively, and in some cases quantitatively, to physiological functions being imaged.

SPECT and PET systems differ because, as their names imply, PET imaging relies upon the characteristic emission of a positron during each disintegration of a positron-emitting isotope, such as carbon-11, nitrogen-13, oxygen-15, fluorine-18, rubidium-82 or gallium-68, and the subsequent emission of two photons in opposite directions along an essentially straight line. SPECT systems rely upon the emission of a single photon that characterizes the decay of certain other isotopes, such as technetium-99m, iodine-123, thallium-201 and xenon-133.

If two photon detectors in a PET system, normally comprising scintillating crystals and photomultiplier tubes in an appropriate spatial relationship, sense the arrival of two photons within a predetermined time interval (i.e., in "coincidence"), it is assumed that a disintegration occurred in a volume between those two photon detectors. This requirement for coincidence establishes an "electronic collimation" for PET systems and eliminates the need for mechanical collimation within a transaxial plane defined by the photon detectors. The spatial resolution of PET systems in the transverse plane (i.e., a measure of the ability or uncertainty of the system to resolve small objects) is primarily dependent on the intrinsic resolution of the photon detectors. Intrinsic resolution represents a limit on the system resolving power and the possible resolution in a reconstructed image with sufficient image data. In such systems the intrinsic spatial resolution normally is stated to be a percentage (e.g., 50 to 60 percent) of the crystal size. These systems are described in the Ter-Pogossian, Wong et al, Burnham et al and Casey et al patents and publications listed above.

SPECT systems also use scintillating crystals and photomultiplier tubes as photon detectors. However, as SPECT systems rely on the emission of single photons, they can not benefit from PET's inherent electronic collimation. Rather a mechanical collimator between the photon detectors and an object being imaged limits the photons that are received by the photon detectors. More specifically, the collimator defines a number of sampling volumes through openings in the collimator that define a photon aperture. Each photon detector "sees" through such a photon aperture in the collimator only that sampling volume that lies along a corresponding sampling axis. If a photon emitted from the sampling volume travels along the sampling axis toward the collimator opening, it passes through the collimator into the corresponding photon detector. The collimator blocks photons emitted from other sites and along other directions from reaching that photon detector.

Originally discrete detector banks and conventional Anger cameras were adapted to SPECT imaging by mounting photon detectors as a head on a rotatable gantry. This gave rise to "moving detector head" systems. In such moving detector head systems, one or more detector heads including a collimator and a photon detector comprising a large flat scintillating crystal, or multiple small crystals, and photomultiplier tubes move and rotate around an object to be imaged. The photon detector localizes a scintillation event in the crystal with sufficient precision to associate each scintillation event with a specific one of the sampling volumes defined by the collimator. The head or heads rotate to sample the emitted photons from the object from many different directions. Electronics use the signals from the photomultiplier tubes to localize each scintillation event on the face of the detector head. Acquired data then is reconstructed into a tomographic image or multiple planar tomographic images each corresponding to a thin slice of the object being imaged.

More recently "fixed detector ring" systems have been developed with a stationary ring of, or cylindrical arrangement of, photon detectors in a two-dimensional form. In such systems, a rotating collimator defines, either by hardware or software means, a two-dimensional matrix of imaging positions about a cylinder while photon detectors, comprising one or more scintillating crystals and photomultiplier tubes, are disposed about the collimator's periphery. These systems define either a single transaxial planar slice or multiple, axially displaced, transaxial planar slices that tomographic image can be formed to represent the distribution of the isotope in a corresponding portion of the body.

Williams et al introduced a single-slice SPECT system of the "fixed detector ring" type. The Hattori patent also discloses a similar system with a different collimator design. In both systems, a single photon detector, including a crystal and photomultiplier tube, is associated with each imaging position in the matrix. Rogers et al and Genna et al disclose a geometry with a fixed cylindrical two-dimensional position-sensitive detector system for multi-slice imaging capability.

According to the disclosures in the Genna patent and publication, for example, a multi-slice SPECT system, also of the "fixed detector ring" type, comprises a collimator with a basically parallel hole configuration in the transaxial plane and a photon detector including a single cylindrical crystal around the collimator and large photomultiplier tubes about the periphery of the single crystal. Digital electronics apply a position determination algorithm, similar to that used in Anger logic to the information gathered by the photomultiplier tubes. These electronics localize each event to a imaging position and its associated sampling volume in a particular transaxial plane. Rogers et al describe a system comprising multiple flat modular scintillation cameras to form a polygonal cylinder for the position sensitive photon detection and a rotating slit collimator.

In all these systems each photomultiplier tube is associated with a number of imaging positions in the matrix. In such variants of gamma cameras the relationship between the spatial resolutions of the system, the collimator and the photon detectors can be given by:

$$R_s^2 = (R_i^2 + R_c^2)$$ Eq. 1 where $R_s$ is the spatial resolution for the detector system, $R_i$ is the intrinsic resolution of a photon detector and $R_c$ is the collimator resolution, all in terms of the full-width at half-maximum (FWHM) of a line spread function (LSF) or the uncertainty of localization. In these gamma cameras using position sensing logic, the system resolution relies equally on both the collimator and intrinsic resolutions as defined in Eq. 1. In accordance with Eq. 1, in PET systems with no mechanical collimator, the electronic collimation basically has little uncertainty in defining the direction of photons, (i.e. as an approximation, $R_c \rightarrow 0$), so the detector system spatial resolution is entirely dependent upon the intrinsic spatial resolution of the detectors (i.e, $R_s = R_i$).

Thus, both intrinsic and collimator resolution influence the detector system spatial resolution in each of the foregoing references. The intrinsic resolution of the photon detectors was generally comparable to or better than the resolution of the collimator over an effective collimation and SPECT imaging range (i.e., $R_i \leq R_c$). However, improvements in collimator resolution have been limited because such improvements generally are offset by decreases in system sensitivity. Thus, most of the effort for improving detector system spatial resolution has been directed to improving the intrinsic resolution of the photon detectors.

The accuracy of position determination in a position sensitive scintillating crystal system depends upon the spatial resolving capability of the detector with respect to multiple scintillation events that occur within the crystal. In gamma camera systems, each scintillation event produces responses in several photomultiplier tubes simultaneously. Over time the position determinations of those events within the crystal that occur at exactly the same interaction site have an uncertainty caused by the statistical variation of photon distribution among the photomultiplier tubes involved; that is, a map of the positions produced by the electronics will be dispersed for scintillation events actually occurring at the same site within the crystal. The degree of dispersion determines the intrinsic resolution ($R_i$) of the photon detector system and acts to broaden the system resolution ($R_s$) as predicted in Eq. 1.

Moreover, the uncertainty or dispersion of determined positions from adjacent imaging or collimator positions can cause overlap of data from different sites and produce significant crossover or mixing of the identifications of sampling volumes. Work to improve the intrinsic resolution has continued and continues even though it has been realized improved intrinsic resolution of a photon detector involves compromises. Specifically, improving intrinsic resolution complicates calibration procedures and correction schemes and, in some applications, can introduce limits on counting rates (i.e., the rate at which scintillation events can be recorded). If an error exists in a correction scheme or calibration procedure or a counting rate is exceeded, the resulting images could be distorted.

The Chang et al patent and publication disclose a fixed detector ring system with a single ring of collimator modules for producing a single tomographic slice. The collimator comprises a series of focused collimator modules each of which define a sampling volume; and the in-plane spatial cross-section of these sampling volumes directly determines the in-plane detector system resolution. Each collimator module also defines one imaging position in the ring. Photon detectors, comprising a single crystal and photomultiplier tube for each collimator module position, localize the collimator module and corresponding sampling volume associated with each scintillation event.

Several problems are introduced if this approach is expanded into a multiple ring configuration for imaging several planar slices simultaneously. First, the number of collimator module positions, that correspond to imaging positions in a matrix, increase proportionally with the number of rings. A corresponding increase is required in the number of photomultiplier tubes, thereby making the system more costly. Moreover, the physical size of available photomultiplier tubes limits the packing of adjacent photomultiplier tubes and has a negative impact on the overall system resolution or sensitivity. Thus, it is desirable to produce such a SPECT system in which the photomultiplier tube size is not a factor in system performance and in which photomultiplier tube costs are reduced. Moreover, it is desirable to produce a system that is adapted for implementation with other photon detector schemes.

A variety of position decoding systems have been suggested for SPECT and PET systems. In these systems the intrinsic spatial resolution of the detectors in the image plane either (1) determines detector system spatial resolution because $R_s = R_i$ when $R_c = 0$ as in PET systems, or (2) strongly influences the detector spatial resolution as in prior gamma camera based SPECT systems. None of these systems suggests the use of their disclosed detector systems in a single-slice system described in the Chang et al references where the spatial resolution of the detector system depends primarily upon the spatial resolution of the collimator (i.e., $R_s = R_c$). In a design as disclosed in the Chang et al references Eq. 1 does not apply, because each detector in the transverse plane is not position sensitive. In addition, the collimator module is a discrete unit quite different from a large conventional gamma camera collimator.

SUMMARY

Therefore it is an object of this invention to provide an improved multi-slice stationary detector single photon emission computed tomography system wherein the detector system resolution in each transaxial plane depends primarily on the spatial resolution of the collimator in each transaxial plane.

Another object of this invention is to provide such an improved stationary detector multi-slice single photon emission computed tomography system in which the collimator is adapted for operation with a wide variety of detector configurations.

Still another object of this invention is to provide such an improved stationary detector multi-slice single photon emission computed tomography system adapted for a variety of collimators.

Still another object of this invention is to provide such an improved multi-slice single photon emission computed tomography system in which detector system costs are reduced.

Still another object of this invention is to provide such an improved multi-slice single photon emission computed tomography system in which localization of a scintillation event is simplified.

Yet still another object of this invention is to provide an improved multi-slice single photon emission computed tomography system that can operate at improved counting rates.

In accordance with this invention, a multi-slice single photon emission computed tomography system comprises an annular collimator means with individual modules arranged around the ring and focused in a transaxial image plane with a spatial resolution over an effective imaging area that determines the spatial resolution for the detector system. The collimator extends axially over all the transaxial image planes to collimate photons from each image plane. The collimator rotates within a stationary cylindrical photon detector system that defines discrete imaging positions around the cylinder for each imaging plane, with one imaging position corresponding to each azimuthal collimator module position in the imaging plane. The photon detector system generates sets of electrical signals that merely distinguish between adjacent imaging positions in a plane. These signals, plus those representing collimator position, identify a specific collimator module and image plane and, in turn, a specific imaging volume that is the site of a photon emission all without introducing complex calibration and correction procedures and without limiting the system counting rate.

This invention is pointed out with particularity in the appended claims. The above and further objects and advantages of this invention as well as further details of the construction and operation of specific embodiments of this invention may be better understood by referring to the following detailed description taken in conjunction with the accompanying drawings.

BRIEF DESCRIPTION OF THE DRAWINGS

FIG. 1 comprises FIG. 1A, a perspective view of a portion of a single photon emission computed tomography system constructed in accordance with this invention and FIG. 1B, a detailed section of the system in FIG. 1A;

FIG. 2 is a block diagram of elements and circuits associated with the system of FIG. 1;

FIG. 3 illustrates an embodiment of this invention in which FIG. 3A depicts a scintillation crystal detector that can be used in the system of FIG. 1; FIG. 3B is a cross section that is useful in understanding some of the relationships of the system; FIG. 3C is a top plan view illustrating the relationship between a number of such detectors and photomultiplier tubes; and FIG. 3D is a section taken along lines 3D—3D in FIG. 3C;

FIG. 4 is a block diagram of the decoding logic shown in FIG. 2 that is particularly adapted for use in this invention;

FIG. 5 comprises FIGS. 5A, 5B and 5C that are, respectively, top, axial and end views of a section of one embodiment of a SPECT system comprising crystals and photomultiplier tubes for producing image planes of selected thickness; and FIG. 6 comprises FIGS. 6A, 6B and 6C that are respectively, top, axial and end views of a section of another embodiment of a SPECT system comprising crystals and photomultiplier tubes for producing image planes of preset thickness; and FIG. 7 depicts collimator arrangements in the axial direction and corresponding tomographic slice profiles that can be implemented in a system constructed in accordance with this invention with FIG. 7A showing a focused collimator and its slice profiles and FIG. 7B, a parallel hole collimator with its slice profiles.

DETAILED DESCRIPTION

Figure 3:
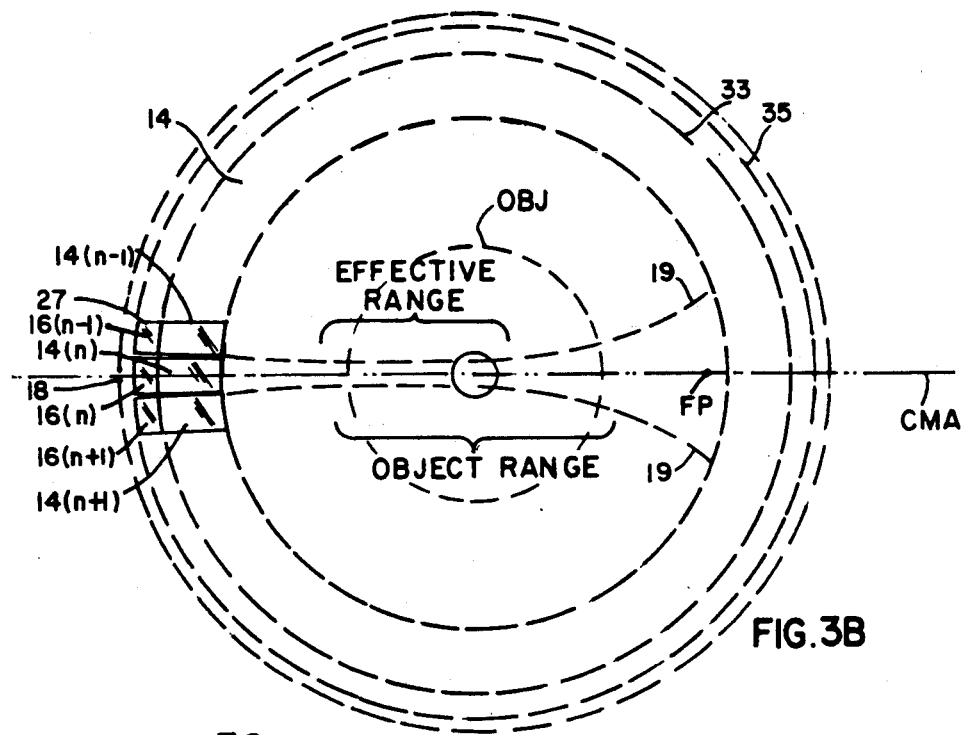
Figure 3:
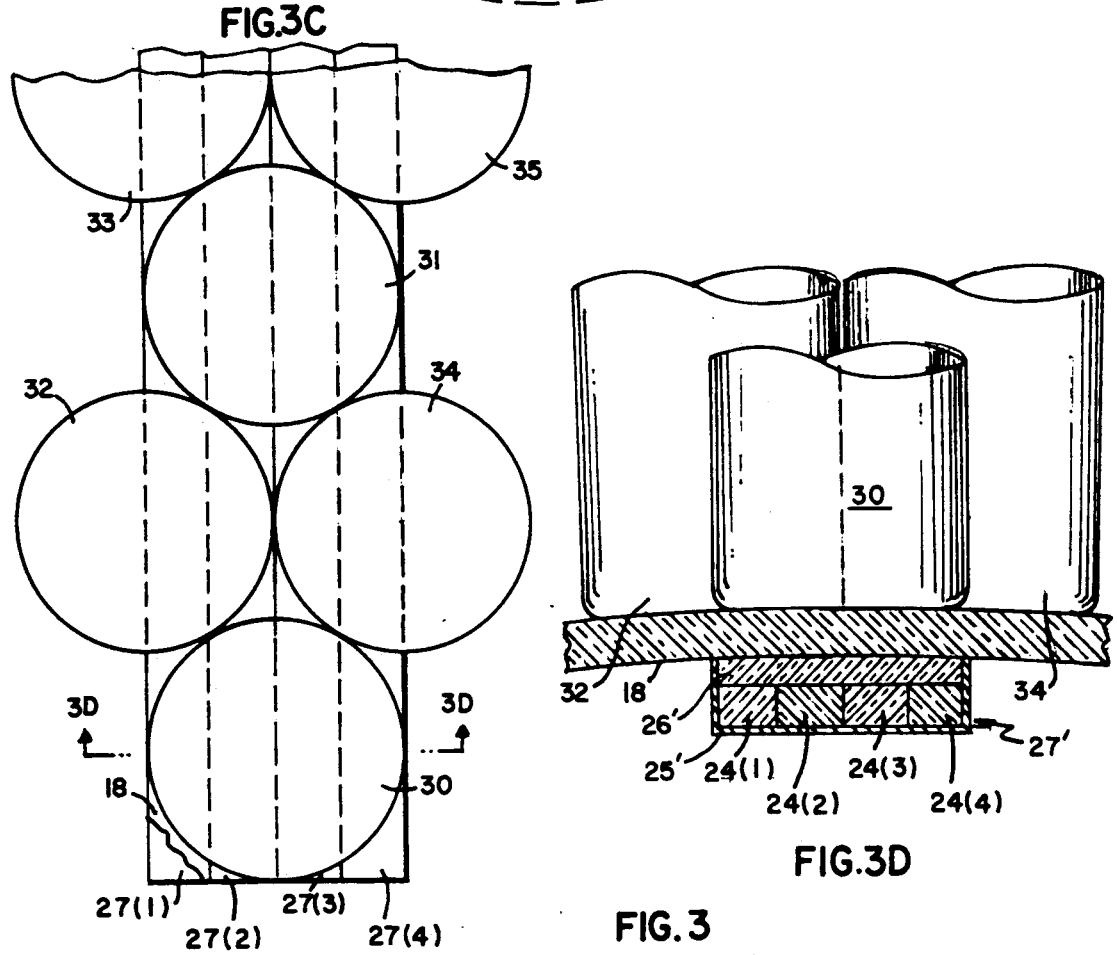

As shown in FIG. 1, a single photon emission computed tomography (SPECT) system includes a photon detector system 10 that includes a cylindrical collimator 11 mounted for rotation by a mechanism, represented by a ring gear 12 attached to the collimator 11 and a motor drive and pinion 13, about a central axis (i.e., a Z-axis) 15. The collimator 11 comprises a series of collimator rings; FIG. 1 shows four rings 14(A), 14(B), 14(C), 14(D); the actual number of rings will depend upon the objectives for a specific application. The rings 14(A) through 14(D) define co-planar transaxial image volumes, so the SPECT detector system 10 produces tomographic images representing the distribution of a radioisotope in corresponding, axially displaced planar slices or thin sections through an object located within the volume defined by the collimator rings 14. The SPECT detector system 10 also includes a stationary photon detector shown in more detail in FIG. 1B, that normally is formed with scintillator crystal detector 16 about the collimator 11, photomultiplier tubes 17 around the crystal detectors 16, and a light guide 18 between the crystal detectors 16 and photomultiplier tubes 17.

In one embodiment of this invention, and for purposes of discussion, the collimator 11 is constructed in accordance with U.S. Pat. No. 4,478,328. As shown in FIGS. 1A and 1B, each of the collimator rings such as ring 14A, comprises discrete collimator modules 14(1), ... 14(n-1), 14(n), 14(n+1). ...

Each collimator module, such as 14(n), is formed with an array of channels that define a focused collimator module with an appropriate focal length. Each of the collimator modules 14 defines a discreet sampling volume along a central imaging axis through the collimator module that has a substantially uniform transverse cross-section in the effective range of collimation (effective sampling volume) in the image plane through the object to be imaged. This transverse cross-section corresponds to the detector system in-plane spatial resolution and determines the reconstructed image resolution for the SPECT system.

Each collimator module has a cross-section in a plane normal to its module imaging axis that is greater than the cross sectional area of the effective sampling volume. For example, a collimator module with a base dimension of 10 mm × 10 mm can produce an in-plane spatial resolution in the order of 6 mm to 7 mm. This of course means that the sampling volumes are nominally spaced from one another. However, as described in the foregoing patent, the drive and pinion 13 and ring gear 12 increment the collimator 11 through a revolution during an image acquistion to sample an object fully.

Referring to FIG. 1B the collimator is oriented with collimator module 14(n) in register with a discrete crystal detector 16(n). The detectors 16(1), ... 16(n−1), 16(n), 16(n+1). .. define discrete, azimuthal imaging positions around the collimator ring 14(A). Moreover, each imaging position defined by a detector 16(i) corresponds to one position of a collimator module 14(1). .. 14(n−1), 14(n), 14(n+1). ... When the collimator 11 is stepped one postion counterclockwise by the mechanism represented by ring gear 12 and drive 13 in FIG. 1A, the collimator module 14(n) will be in register with the crystal detector 16(n+1). However, there will still be a correspondence between one detector imaging position and one collimator module position, albeit a different collimator module.

The stationary crystal detectors 16 are arranged about the collimator 11 to convert those photons that are emitted from the object along the general direction of the module imaging axis through a collimator module into a detectable alternate energy form, while the photomultipliers 17 monitor the crystal detectors 16 to produce a set of electrical signals that identify a particular crystal detector 16 that has received a photon.

Referring to FIG. 2, as the drive and pinion 13 rotates the collimator 11 in FIG. 1, a collimator position sensor 20 generates a position code in the form of signals that identify the angular position of the collimator 11 and hence the position of each specific collimator module 14, so the positional relationship of the collimator modules 14 and the crystal detectors 16 in FIG. 1 is specified. For each scintillation event, a detector identification section 21 responds to electrical signals from the photomultiplier tubes 17 by producing a set of signals. Each set of signals, collectively, identifies a crystal detector position both azimuthally around the ring and axially along that azimuthal position and, therefore, a discrete imaging position in a photon detector matrix defined by the collective set of photon detectors. A sampling volume identification section 22 combines the detector and collimator position codes and generates a code that identifies a specific sampling volume for a detected photon. A reconstruction section 23 accumulates these sampling volume identification codes and constructs a final tomographic image using conventional reconstruction techniques. As will be apparent, each of these sections may be implemented by hardware, software or a combination thereof.

FIGS. 3A and 3B illustrate certain dimensional relationships in more detail. As previously indicated, a collimator module, such as module 14(n) in FIG. 3B, can be constructed to provide an in-plane spatial resolution in the order of 6 mm to 7 mm; physically, such a module will cover about 10 mm in physical dimension on the circumference in the image plane; that is, the azimuthal dimension transverse to a collimator module axis CMA for that module will be about 10 mm. With these dimensions, about 100 modules can be disposed about a circle approximately 33 cm in diameter.

As described in the Chang et al patent and publication, each collimator module 14 is focused at a point FP. With this rather long focal length, the transverse spatial resolution of a collimator module 14 through an object outline OBJ centered on the system axis 15 is substantially constant over an effective collimator range that is the distance from the periphery of the imaging volume to the central axis 15 as indicated by the dashed lines 19 in FIG. 3B. It is this spatial resolution of the collimator module that defines the overall in-plane transverse spatial resolution for the SPECT system.

As also indicated in FIGS. 1A, 1B and 3B, the crystal detectors 16 comprise a plurality of discrete units 16(1), ... 16(n) ... disposed about the collimator modules 14. In the transaxial plane, there is a basic correspondence of one discrete detector at each azimuthal position and for each collimator module, except for a few detectors that are blocked by corner wedges, as disclosed by the Chang et al references. In one embodiment, for example, 96 azimuthal crystal detector positions could be associated with 80 collimator modules around the collimator ring 14. In this configuration, each crystal detector 16 need only have a physical dimension and resolving capability that are matched to a collimator module to convert a scintillation event into an identification of a crystal detector 16 and, thereby, the collimator module 14 between that crystal detector and the object.

FIG. 3A depicts a single crystal detector 16 that adapts the single ring system of U.S. Pat. No. 4,748,328 to a multi-ring system without a concomitant increase in number of photomultiplier tubes all in accordance with this invention. Each detector, such as detector 16, is elongated axially (i.e., parallel to the axis 15 in FIGS. 1A, 1B and 3B) to form a bar as shown in FIG. 3A. In a specific embodiment, a rectangular sodium iodide crystal 24 is encased in a metal shield 25. A glass window 26 seals the top of the bar and allows light, produced by scintillation in the crystal 24, to pass to photomultiplier tubes, such as photomultiplier tube 17 that is located over the glass window 26 on a light guide 18. The crystal 24, shield 25 and glass window 26 constitute a single bar detector 27 that is axially longer than the required axial extent of the images to be obtained, as discussed later. One specific bar-detector has been constructed with a sodium iodide crystal that is 10 mm wide by 12.5 mm high by 180 mm long. In this configuration the overall collimator module dimension is about 10 mm transverse to the collimator module axis CMA and 30 mm along the axis CMA shown in FIG. 3B.

As shown in FIG. 3B, the bar detectors 27 are arranged in a cylindrical pattern to extend axially (i.e., a cylinder that is coaxial with the axis 15. A light guide 18 between the bar detectors 27 and the photomultiplier tubes transfers light from the bar detector to plural photomultiplier tubes. In FIGS. 1A and 1B, the light guide is depicted as a single cylindrical unit. In FIGS. 3C and 3D, a portion of light guide 18 is located adjacent four crystal detectors 24(1), 24(2), 24(3) and 24(4) that are grouped in a module 27' that is approximately 50 mm wide by 180 mm long. The crystals are housed in a single metal shield 25' and are covered by a single glass window 26'. Although the crystals are shown in contiguous relationship, the module normally will include reflective material between adjacent crystals. An array of round photomultiplier tubes including photomultiplier tubes 30 through 35 are packed over the bar detectors 27' in a hexagonal pattern on the cylindrical light guide 18. The photomultiplier tubes 30 through 35 and light guide 18 are interfaced for good light transmission, as known, so the light guide 18 distributes light from the bar detectors 24 to the array of photomultipliers optically associated with the bar detector module.

As apparent, as the site of a scintillation event moves from one detector to another, the levels of output signals from the involved photomultiplier tubes will vary. As the site of a scintillation moves axially along any specific bar detector, the relative light at each of the axially displaced photomultiplier tubes also varies. Thus, a position sensing algorithm such as used in Anger logic systems, can be embodied by including hardware, software or a combination thereof, to convert the output signals from the various photomultiplier tubes into signals that identify both a specific one of the bar detectors 27' and an axial position along that specific bar detector 27' thereby locating and identifying an imaging position in the matrix as the site of a scintillation event. The position sensing algorithm that performs this conversion was previously discussed with respect to the detector identification section 21 in FIG. 2. Hence, image data for discrete multiple planes can be acquired by electronically dividing the axial length of the bar detectors 27 into a series of smaller discrete areas or a one-dimensional matrix along the axis 15. A second one-dimensional matrix of imaging positions is defined by bar-detectors distributed azimuthally about the ring. Thus, the bar detectors and a linear position sensing form a two-dimensional matrix of imaging positions defined by axial and azimuthal coordinates. It will also be apparent that the number of imaging positions in the matrix exceeds the number of photomultiplier tubes, so the increased capability has been achieved without a concomitant increase in the number of photomultiplier tubes.

FIG. 4 is a block diagram that illustrates circuitry for localizing the site of each scintillation event to a specific imaging position in the matrix. The output signals from four photomultiplier tubes 17, shown as being displaced along the axis, are interfaced with the light guide 18 over associated with a bar-detector 27'.

The circuitry in FIG. 4 uses a "centroid" algorithm that is a digital version of Anger logic analysis to identify the axial position of a scintillation event in a bar-detector 27 from digital codes. More specifically, amplifiers 36 shape and couple each signal to the input of a summing circuit 37 and an analog-to-digital converter 40. The output from the summing circuit 37 passes through a single-channel analyzer (SCA) 41 and a delay circuit 42 to trigger the analog-to-digital converter 40 and thereby sample the output from the photomultiplier tubes. The resulting output from the analog-to-digital converter 40 is applied to a processing unit 43. The processing unit 43 performs the centroid weighting calculation and a linearity correction to produce the axial position, i.e., the position along the axis 15 relative to the center of the detector module 27'. More specifically, in accordance with the centroid method the axial position is calculated according to:

$$Z = \Sigma W_i E_i / \Sigma E_i \qquad \text{Eq. 2}$$

where $W_i$ is a distance weighting factor and $E_i$ is the output voltage from a photomultiplier along the bar. The processing unit 43 also uses the recorded information in a similar fashion to identify the azimuthal position of a specific bar detector.

FIG. 5 including FIGS. 5A, 5B and 5C, depicts a preferred modular bar-detector arrangement that is particularly adapted for implementation with square photomultiplier tubes. A bar detector module 46 combines several crystals 24' in a metal shield 25' with the opening sealed by a glass window 26', as in FIG. 3. A light guide segment 47 is affixed to the glass window 26'. The light guide segment 47 has two tapered upper surfaces 47a and 47b, with the taper dependent upon the system geometry. For example, if 96 crystal detectors are positioned about the perimeter of the system, each set of four detectors could be offset by 15° from the next, in which case, the surfaces would be inclined 7.5° to the horizontal and 165° to each other. Analogous tapering of the sides will enable adjacent modules 46 to fit closely with respect to each other. Moreover, the module shown in FIGS. 5A, 5B and 5C is shown as having plane surfaces. In actual practice, the surface of the metal shield shield 25' and corresponding surfaces of the crystals 24' could be curved to conform more closely to the outer cylindrical surface of the collimator module 14.

Six square photomultiplier tubes 50 through 55 are positioned along the Z-axis 15 in two axial rows of three tubes each. Each axial row of three photomultiplier tubes, such as photomultiplier tubes 50, 51 and 52, receive light from eight bar-detectors 27 as they lie over two adjacent four-bar-detector modules 46. 46a however, edges 47c and 47d of the light guide segment 47 constitute optical barriers, so light from one specific detector module 46 and light guide segment 47 is limited to those photomultiplier tubes that overlie that light guide 47.

With this configuration, the position of each scintillation event along a bar-detector (i.e., the axial or Z-axis position) can be calculated with the analog or digital versions of Anger logic such as described previously with respect to FIG. 4. Furthermore, the relative distribution of the light collected in two sets of axially aligned rows of photomultiplier tubes (e.g., 50 and 53)

localizes the specific bar detector 27' that is involved in the event. As will be apparent, the discrete nature of the bar detectors 27' in the transaxial plane reduces, to a low level, the uncertainty in distinguishing events in adjacent bar detectors. Measurements indicate that these uncertainties are greatly reduced particularly for those photons that interact near the physical boundary between adjacent bar-detectors. Moreover it is only necessary to resolve the location on the circumference to about 10 mm azimuthally in the plane so that significant changes in signal levels can be used to discriminate among the individual bar detectors 27, thereby making the positioning determination less sensitive to errors introduced by electronics drift, noise or other extraneous influences.

It has been found that arrangements of bar-detectors based upon the configuration of FIGS. 5A though 5C impose a limitation on the extent of imaging along the Z-axis 15. The limit is approximately the area between the centers of the end photomultiplier tubes. This is shown as active area 56 in FIG. 5A. Thus only about 60% of the bar detectors 27' correspond to the actual Z-axis imaging distance. For example, a bar detector that is 150 mm long will have an active area 56 of about 90 mm to 95 mm centered on the Z-axis 15.

With the bar detector approach of FIG. 5, a collimator of focused design can be maintained in the transaxial planes but provide parallel hole collimation in the axial direction. Then the digitization of the axial position signal can be adapted to provide variable numbers of transaxial planes of selectable width and axial position as described later.

FIG. 6 including FIGS. 6A, 6B and 6C depicts another embodiment of a SPECT system with shared photomultiplier tubes in which system spatial resolution is determined primarily by the collimator resolution in both the in-plane and axial dimensions. This approach will be particularly useful in systems that require multiple, equally spaced, noncontiguous slices. The SPECT system in FIGS. 6A, 6B and 6C comprises a plurality of photon detector modules 60 that comprise thirty-two discrete crystals corresponding to imaging positions in a matrix with four azimuthally defined (i.e., parallel to the axis 15) rows and eight axially displaced rows. Each module 60 can register with thirty-two collimator modules in the collimator 11, also disposed in eight parallel transaxial planes, or rings 14(A)... 14(H). Thus, each detector module 60 is associated with a section of imaging positions in a photon detector matrix defined by 4 azimuthal and 8 axial position coordinates.

More specifically, a detector module 60 includes a metal shield 25" that contains 32 discrete crystals 24" deposited in a 4×8 matrix. As previously indicated, there may be a light reflecting material deposited between adjacent crystals. A glass window 26" closes the open metal shield 25" and seals the crystals 24" within the metal shield 25". With this configuration, each circumferential row defines an image slice, so a SPECT system with the module 60 will acquire data from eight predetermined image slices simultaneously. Moreover, each of the collimator modules will be in register with a crystal (i.e., an imaging position on the photon detector matrix) in both the axial and azimuthal positions.

Four photomultiplier tubes 61, 62, 63 and 64 are associated with the detector module 60. Specifically, one-half of each photomultiplier tube overlies one-quarter of the detector module 60, as apparent in FIG. 6A. A light guide 66, formed segments, lies between the photomultiplier tubes 61 through 64 and the detector module 60. This light guide 66 is a polyhedron with a bottom surface in contact with the glass window 26" of the detector module 60. The side vertical surfaces define discrete optical barriers that block any light from transferring to an adjacent light guide.

An upper portion of the light guide 67 comprises four planar surfaces 67a through 67c shown in FIGS. 6A through 6C and a fourth surface that does not appear in the drawings. Each surface is normal to the axis of a corresponding photomultiplier tube. In the circumferential direction, as shown in FIG. 6B, the angle is determined by the number of detector modules that form a ring. From the side view shown in FIG. 6C, the light guide is sloped up to 10° with respect to the horizontal. These planes "aim" each photomultiplier tube toward the "center" of their respective active fields of view.

This embodiment in FIGS. 6A, 6B and 6C eliminates the extension of crystal material beyond the active imaging field along the Z-axis 15 that characterizes the bar detectors in FIGS. 5A, 5B and 5C. Moreover, this embodiment in FIG. 6, with its eased requirement for intrinsic detector resolution, permits the position of each detector to be ascertained merely by monitoring the ratio of signals from the photomultiplier tubes 61 through 64. Experimental results indicate that axial rows, such as axial rows 60a and 60b, can be identified by examining the ratio of (1) the sum of the signals from photomultiplier tubes 61 and 63 to (2) the sum of the signals from photomultiplier tubes 62 and 64. Similarly, the circumferential rows (i.e., rows 60(1)through 60(8)) can be distinguished and localized by examining the ratio of (1) the sum of the signals from photomultiplier tubes 61 and 62 to (2) the sum of the signals from photomultiplier tubes 63 and 64.

A further improvement in positioning accuracy in the axial direction can be attained by establishing air or other optical barriers in the light guide 18 to improve the differential of the dispersal of light to the photomultiplier tubes. In FIG. 6C, such barriers are produced by segmenting the light guide 66 axially. In this embodiment end segments 66a and 66b lie over the crystals on the end rings of collimator modules 14A and 14H and the corresponding crystal detectors. A central section 66c covers the remaining six collimator rings 14B through 14G. This improves the crystal detector identification at both ends of the axial direction. Other barriers, masks, reflective surfaces or even space may be incorporated into the light guide to establish better light differentiation among the photomultiplier tubes and thereby improve axial position decoding.

This improved ratio of active imaging to photomultiplier tube area is also due in part to the fact that the axial spatial resolution for the detector system in this embodiment depends upon the axial resolution of the collimator modules. With 80 collimator modules and 96 detectors in each imaging plane, this system defines an imaging matrix with 96 azimuthal imaging positions in each of eight (8) imaging planes for a total of 768 imaging positions for 640 collimator modules. However, the system only requires 48 two-inch or 32 three-inch photomultiplier tubes. Thus, this embodiment again utilizes collimators to establish the detector system spatial resolution, eases the requirements on the intrinsic resolution of the detector system and enables an increase in the number of imaging positions without an concomitant increase in the number of photomultiplier tubes.

Certain aspects of the SPECT systems in FIGS. 5 and 6 can be combined, for example, to image a greater number of slices over a larger z-axis dimension. More specifically, a number of collimator rings 14 and a like number of detector rings 16 can be added to the collimator rings 14 and photon detector rings 16 shown in FIG. 6 to extend its axial imaging area. This collimator-photon detector assembly then can be substituted for the collimator 14 and bar detectors 27 in FIG. 5, such that the three rings of photomultiplier tubes and the window 47 in FIG. 5 overlie the new collimator-photon detector assembly. In this embodiment, the active imaging area 56 is coextensive with the array of crystal detectors 16 and the photomultiplier tubes. Each photomultiplier tube is coextensive with a section of the crystal detectors 16 and the middle ring of photomultiplier tubes is centered between the end rings. Some additional axial length could be obtained by adding even more rings of collimators and detectors and by spacing the rings of photomultiplier tubes.

As previously indicated, further flexibility can be achieved by matching different collimators to the photon detectors shown in FIGS. 5 and 6 as well as other photon detector embodiments. FIGS. 7A, and 7B for example, depicts a cross section of a collimator 11 as shown in FIG. 6. Each collimator module, such as module 16(n), is focused in the axial direction (along the axis 15). After reconstruction the tomographic images will have a slice profile of substantially constant thickness, as shown by slices 80(A) through 80(H). These slices are not contiguous. However, the gaps can be filled by introducing relative motion between the patient and the system that corresponds to about one-half the axial distance between slices. This configuration may change the overall sensitivity in each slice, but is appropriate where constant slice thickness through the image is more important than full axial sampling. It is also possible to utilize such a collimator with the bar detector approach shown in FIG. 5, provided the active area 56 is coextensive with the z-axis extent of the collimator modules.

FIG. 7B shows a parallel hole collimator 14 that is particularly adapted for the bar-detector configuration shown in FIG. 5. In this embodiment, the intrinsic resolution of the bar detector, in the axial direction, enables the system to locate each event to a finely sampled imaging position defined by matrix behind the parallel hole collimator. For example, sample planes 81, 82 and 83 are defined by imaging positions in the matrix. Each of these sample slices, such as sample slice 84 associated with imaging position 85, has a relatively uniform resolution in the transaxial plane. However, each slice has a slightly convex cross section in the axial plane. Adjacent sample planes overlap to some extent. As a result, contiguous axial sampling is achieved. Moreover, during reconstruction multiple, adjacent sample planes can be combined to from slices of desired thickness.

A collimator with a converging configuration in the axial direction can also be substituted. With a converging configuration, all the holes in the axial direction are focused to a single point which is not necessarily the focal point of the individual collimators in the transaxial direction. This collimator, similar to an astigmatic collimator or a cone beam collimator in concept, increases sensitivity, but requires special reconstruction techniques for artifact free image reconstructions.

In general, these embodiments are illustrative of a multi-slice SPECT system in which at least the in-plane spatial resolution of the system is determined primarily by the resolution of the collimator modules so that the requirements for the intrinsic resolution of the detectors is relaxed in a way that the conversion to a multi-slice system with an increase in imaging positions, but without a concomitant increase in the number of photomultiplier tubes or similar conversion elements. This concept may also be extended in the axial direction.

While the disclosure has been made in terms of specific embodiments, a number of variations are possible. In addition to being implemented with a variety of collimators, this invention is also adopted for use with photon detectors other than those that include scintillating crystals and photomultiplier tubes. Multi-wire and ionization chambers and photodiodes can be adapted to define the imaging positions of the photon detector matrix of this invention because the relaxed requirements for detector intrinsic resolution make these technologies more readily adapted to SPECT systems. In addition, certain portions of the disclosure describe the components of the SPECT system with reference to specific dimensions for clarity. Elements can be formed with other dimensions and relationships.

Thus, while this invention has been disclosed in terms of certain embodiments, it will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A single photon emission computed tomography system for producing plural tomographic images transverse to an axis representing the distribution of a photon-emitting radioisotope in corresponding axially displaced, transverse imaging planes through a body, said system including a detector system having a given spatial resolution in the planes and comprising:

A. a plurality of stationary discrete photon responsive means defining a cylindrical photon detector matrix of imaging positions coaxially with the body and said axis for converting photons into electrical signals, each said imaging position in said matrix defined by one of a predetermined number of azimuthally discrete imaging positions about the axis and by an axial position of the imaging plane along the axis, the imaging positions at a given azimuthally discrete position coextensive with the transverse imaging planes constituting an imaging matrix row, B. matrix position identification means for generating first and second sets of electrical signals that collectively identify, for each photon that is intercepted in said photon responsive means, an imaging position in said photon detector matrix, C. a plurality of collimator module means between the body being imaged and said photon responsive means, each said collimator module means having an outer dimension coextensive with an azimuthal imaging position and having channel means coextensive with only a portion of a corresponding azimuthal imaging position, said first set of signals from said matrix position identification means localizing for each photon only the discrete azimuthal position for the detector, each said collimator module channel means being focused to define a discrete sampling volume with a dimensions that is less than the dimension of an azimuthally discrete matrix position and passing therethrough to an associated one of said azimuthally discrete photon detector matrix positions only photons emitted from the corresponding sampling volume along the general direction of collimator module axis whereby said collimator module means determine the in-plane spatial resolution independently of said first signals from said matrix position identification means, D. collimator incrementing means for incrementing said plurality of collimator module means past said stationary photon responsive means through a plurality of collimator positions and for generating collimator position identification signals that identify each of said collimating module means positions, and E. processing means connected to said matrix position identification means and said collimator incrementing means for identifying the specific sampling volume from which a photon emerged, the identifications of successive sampling volumes providing data for the reconstruction of the tomographic images.

2. A single photon emission computed tomography system as recited in claim 1 wherein each said discrete photon responsive means is disposed in each imaging position of said photon detector matrix and each of said collimator modules is focused to a point both in a transverse plane and axially to define a sampling volume in a discrete image plane, said second set of signals from said matrix position identification means resolving, for each collimator module, only the discrete axial position for the detector, the spatial resolution of each of said collimator modules in the axial and transaxial directions thereby determining the corresponding spatial resolutions of the said detector system independently of said signals for said matrix position identification means.

3. A single photon emission computed tomography system as recited in claim 1 wherein each of said discrete photon responsive means is elongated to form a positionsensitive detector covering multiple axial imaging positions and to respond to any photon reaching all the imaging positions in a corresponding axial row of said photon detector matrix and wherein each of said collimator modules means is coextensive with a said axial extent of the transverse planes, said second signals from matrix position identification means resolving the location of axial imaging positions in the photon detector matrix independently of said collimator module means whereby said collimator module means determine the system in-plane resolution and said photon responsive means and said matrix position identification means as well determine the axial resolution of said detector system.

4. A single photon emission computed tomography system as recited in claim 1 wherein said discrete photon responsive means comprise scintillating crystals means for generating light in response to an interaction of a photon therein and wherein said matrix position identification means comprises:
  i. a plurality of photomultiplier tube means for generating electrical signals in response to light, each said photomultiplier tube means being coextensive with a plurality of said scintillating crystal means;
  ii. light guide means interposed between said scintillating crystal means and said photomultiplier tube means for dispersing light from a photon responsive means to said plurality of said photomultiplier tube means, and
  iii. means responsive to the collective signals from said photomultiplier tube means produced during each scintillation event for locating the site of each scintillation event in an imaging position of photon detector matrix.

5. A single photon emission computed tomography system as recited in claim 4 wherein said light guide means comprises a continuous light conduction means interposed between all of said scintillating crystal means and said photomultiplier means.

6. A single photon emission computed tomography system as recited in claim 4 wherein each of said discrete photon detector means includes a scintillating crystal means at each azimuthally discrete position and each said scintillating crystal means extends over all the imaging positions in a corresponding axial row and wherein each of said photomultiplier tube means is coextensive with a plurality of said axial and azimuthally discrete positions in said photon detector matrix, said light guide means comprising plural discrete light guides for coupling light from a predetermined set of said discrete photon detector means to a predetermined plurality of said photomultiplier tube means, said matrix position identification means additionally producing signals for localizing each scintillation event axially in said photon detector means.

7. A single photon emission computed tomography system as recited in claim 6 wherein each of said collimator modules means has a photon aperture that is coextensive with all the axial positions in each corresponding azimuthal location of said photon detector matrix, each said collimator module means being focused individually in the transverse planes to define a substantially constant cross-section sampling volume that determines the in-plane detector system spatial resolution.

8. A single photon emission computed tomography system as recited in claim 7 wherein each said collimator module means is constructed with a parallel hole configuration over the axial positions in each corresponding azimuthal discrete position of said photon detector matrix.

9. A single photon emission computed tomography system as recited in claim 7 wherein each said collimator module is constructed in a converging configuration over the axial positions in each corresponding azimuthally discrete position of said photon detector matrix.

10. A single photon emission computed tomography system as recited in claim 4 wherein each of said discrete photon responsive means includes a discrete scintillating crystal means at each imaging position in said photon detector matrix such that each scintillating crystal means is only responsive to a photon reaching a single imaging position in the photon detector matrix and wherein said matrix positioning identification means comprises
  i. a plurality of photomultiplier tube means for generating electrical signals in response to light, each said photomultiplier tube means being coextensive with a plurality of said discrete scintillating crystal means,;
  ii. discrete light guide means interposed between a plurality of said scintillating crystal means and a plurality of said photomultiplier tube means for dispersing light from any of a predetermined plurality of said scintillating crystal means to a predetermined plurality of said photomultiplier tube means, and iii. means responsive to the collective signals from said photomultiplier tube means produced during each scintillation event for locating the site of each scintillation event in an imaging position of said photon detector matrix.

11. A single photon emission computed tomography system as recited in claim 10 wherein said discrete crystal means are grouped into a plurality of detector modules, each said detector module containing an array of discrete crystals and a common glass window, said light guide means comprising a light guide segment that is coextensive with a said window and wherein each of said photomultiplier tube means overlies portions of adjacent modules.

12. A single photon emission computed tomography system as recited in claim 11 wherein each of said collimator module means has a photon aperture that is focused axially whereby said collimator module means determine both the axial and in-plane spatial resolutions for said detector system.

13. A single photon emission computed tomography system as recited in claim 10 wherein said light guide means overlies the entire photon detector matrix and includes optical means for controlling the dispersal of light.

* * * * *